United States Patent
Ding et al.

(10) Patent No.: US 12,318,243 B2
(45) Date of Patent: Jun. 3, 2025

(54) METHOD FOR DETERMINING BLOOD FLOW VELOCITY USING DUAL DIE GROUP AND DOPPLER BLOOD FLOW DETECTION DEVICE

(71) Applicant: SUZHOU SENSUS MEDICAL TECHNOLOGY CO., LTD., Jiangsu (CN)

(72) Inventors: Yan Ding, Suzhou (CN); Dongjun Sun, Suzhou (CN); Runbao He, Suzhou (CN); Yuechun Zhang, Suzhou (CN)

(73) Assignee: SUZHOU SENSUS MEDICAL TECHNOLOGY CO., LTD., Jiangsu (CN)

( * ) Notice: Subject to any disclaimer, the term of this patent is extended or adjusted under 35 U.S.C. 154(b) by 0 days.

(21) Appl. No.: 18/753,524

(22) Filed: Jun. 25, 2024

(65) Prior Publication Data
US 2024/0341718 A1    Oct. 17, 2024

Related U.S. Application Data (63) Continuation of application No. PCT/CN2023/087749, filed on Apr. 12, 2023.

(30) Foreign Application Priority Data

Nov. 24, 2022    (CN) .......................... 202211479824.2

(51) Int. Cl.
*A61B 8/06*    (2006.01)
*A61B 8/00*    (2006.01)

(52) U.S. Cl.
CPC ............... *A61B 8/06* (2013.01); *A61B 8/488* (2013.01)

(58) Field of Classification Search
None
See application file for complete search history.

(56) References Cited

U.S. PATENT DOCUMENTS 5,085,220 A    2/1992   Nudell et al.
2006/0235314 A1*  10/2006  Migliuolo ............ A61B 1/0011
                                            600/549

(Continued)

FOREIGN PATENT DOCUMENTS

CN    1257695 A    6/2000
CN    103169503 A  6/2013

(Continued)

OTHER PUBLICATIONS

Wang et al., "Flexible Doppler ultrasound device for the monitoring of blood flow velocity," Science Advances, vol. 7, No. 44, Oct. 27, 2021, pp. 1-10.

*Primary Examiner* — Jonathan Cwern
(74) *Attorney, Agent, or Firm* — Birch, Stewart, Kolasch & Birch, LLP (57) ABSTRACT

The present disclosure relates to a method for determining blood flow velocity using a dual die group and a Doppler blood flow detection device including a first die group and a second die group placed at different positions of a blood vessel to be detected. The method includes obtaining a first spectrum waveform by detecting the blood vessel to be detected using the first die group, obtaining a second spectrum waveform by detecting the blood vessel to be detected using the second die group, determining a relationship between an actual Doppler angle during detection and a set Doppler angle in the Doppler blood flow detection device according to the first spectrum waveform and the second spectrum waveform, adjusting the first spectrum waveform and the second spectrum waveform according to the deter- (Continued)

mined relationship, and determining a blood flow velocity measurement value based on the adjusted first and second spectrum waveforms.

17 Claims, 6 Drawing Sheets

(56) References Cited

U.S. PATENT DOCUMENTS

| | | | |
|---|---|---|---|
| 2007/0073153 A1 | 3/2007 | Tortol | |
| 2011/0137175 A1* | 6/2011 | Hossack | A61B 8/488 600/454 |
| 2013/0030299 A1 | 1/2013 | Kim | |
| 2013/0197365 A1* | 8/2013 | Baba | A61B 8/54 600/447 |
| 2018/0192996 A1* | 7/2018 | Kobayashi | A61B 8/5223 |
| 2021/0128076 A1* | 5/2021 | Shi | G16H 30/20 |

FOREIGN PATENT DOCUMENTS

| | | |
|---|---|---|
| CN | 108186050 A | 6/2018 |
| CN | 112120734 A | 12/2020 |
| CN | 113367730 A | 9/2021 |
| CN | 115517708 A | 12/2022 |
| JP | 2003-70789 A | 3/2003 |

* cited by examiner

METHOD FOR DETERMINING BLOOD FLOW VELOCITY USING DUAL DIE GROUP AND DOPPLER BLOOD FLOW DETECTION DEVICE

RELATED APPLICATIONS

The present disclosure is a Continuation application of International Application No. PCT/CN2023/087749, filed on Apr. 12, 2023, which claims priority to Chinese patent application No. 202211479824.2, filed on Nov. 24, 2022, entitled "METHOD FOR DETERMINING BLOOD FLOW VELOCITY USING DUAL DIE GROUP AND DOPPLER BLOOD FLOW DETECTION DEVICE", which is incorporated herein by reference in its entirety.

TECHNICAL FIELD

The disclosure relates to the field of medical detection, and in particular, to a method for determining blood flow velocity using a dual die group and a Doppler blood flow detection device.

BACKGROUND

With the development of science and technology, medical detection means are applied to obtain relevant parameters of the human body to assist the doctor to diagnose various diseases that occur in the human body. The blood flow velocity is an important physiological parameter, and many diseases can be reflected by the blood flow velocity.

The basic principle of using the Doppler technology to detect the blood flow velocity is as follows. An ultrasonic probe emits an ultrasonic wave with a certain intensity, and in the condition that the ultrasonic wave meets the flowing blood, scattering may be occurred when the ultrasonic wave meets red blood cells in the blood since the wavelength of the ultrasonic wave is greater than the diameter of the red blood cell. Meanwhile, since the red blood cells are moving, the Doppler frequency shift may occur to the scattered echo signal. The greater the velocity is, the greater the frequency shifts. By analyzing the frequency shift of the echo signal and combining it with the mathematical equation of the Doppler technology, the moving velocity of the red blood cells may be deduced.

Recently, the Doppler blood flow detection device has been widely used to detect blood flow velocity of a patient in the clinical practice. However, in actual use, the measurement result often has certain errors. Especially, when the medical staff's operation is not standard, or the patient moves during a long-term monitoring process, the error of the measurement result may be greater, which may reduce the referenceability of the blood flow velocity measurement result, and may cause the medical staff to misjudge the patient's condition in serious cases.

SUMMARY

In view of the above, embodiments of the present disclosure provides a method for determining blood flow velocity using a dual die group and a Doppler blood flow detection device to solve at least one of the problems existed in the background.

In a first aspect, embodiments of the present disclosure provide a method determining blood flow velocity using a dual die group, applied to a Doppler blood flow detection device, wherein the Doppler blood flow detection device includes a first die group and a second die group placed at different positions of a blood vessel to be detected, the method includes:
obtaining a first spectrum waveform by detecting the blood vessel to be detected using the first die group;
obtaining a second spectrum waveform by detecting the blood vessel to be detected using the second die group;
determining a relationship between an actual Doppler angle during detection and a set Doppler angle in the Doppler blood flow detection device according to the first spectrum waveform and the second spectrum waveform;
adjusting the first spectrum waveform and the second spectrum waveform according to the determined relationship;
determining a blood flow velocity measurement value according to the adjusted first spectrum waveform and the adjusted second spectrum waveform.

In a second aspect, embodiments of the present disclosure provide a Doppler blood flow detection device for implementing any one of the methods of determining blood flow velocity using a dual die group in the first aspect.

Embodiments of the present disclosure provide a method for determining blood flow velocity using a dual die group and a Doppler blood flow detection device. The device includes a first die group and a second die group placed at different positions of a blood vessel to be detected. The method includes obtaining a first spectrum waveform by detecting the blood vessel to be detected using the first die group, obtaining a second spectrum waveform by detecting the blood vessel to be detected using the second die group, determining a relationship between an actual Doppler angle during detection and a set Doppler angle in the Doppler blood flow detection device according to the first spectrum waveform and the second spectrum waveform, adjusting the first spectrum waveform and the second spectrum waveform according to the determined relationship, and determining a blood flow velocity measurement value based on the adjusted first spectrum waveform and the adjusted second spectrum waveform. Thus, the error problem caused by the inconsistency between the angle between the probe and the blood vessel to be detected and the set Doppler angle in the device during actual detection can be avoided, thereby improving the accuracy of the blood flow velocity measurement value.

Additional aspects and advantages of the disclosure will be set forth in part in the following description, and in part will be obvious from the description, or may be learned by the practice of the disclosure.

BRIEF DESCRIPTION OF DRAWINGS

The accompanying drawings are included to provide a further understanding of the present disclosure and constitute a part of the present disclosure. The illustrative embodiments and the descriptions thereof in the present disclosure are used to explain the present disclosure and do not constitute an undue limitation of the present disclosure. In the drawings.

DETAILED DESCRIPTION

To make the technical solutions and advantages of the present disclosure more obvious and understandable, detailed descriptions are given below by enumerating specific embodiments. The accompanying drawings are not necessarily drawn to scale, and local features may be enlarged or reduced to show details of the local features more clearly. Unless defined otherwise, technical and scientific terms used herein have the same meaning as those in the technical field to which the present disclosure belongs.

Unless defined otherwise, technical or scientific terms used herein should have general meanings understood by those skilled in the art to which the present disclosure belongs. The words like "a", "an", "the", "these" and similar words in the present disclosure are not to be construed as limiting in number, which may be in the singular or the plural form. The terms "comprise", "include", "have" and any variations thereof involved in the present disclosure are intended to cover a non-exclusive inclusion, for example, a process, a method, a system, a product, or a device including a series of steps or modules (units) is not limited to the listed steps or modules (units), but may include steps or modules (units) that are not listed or other steps or modules (units) inherent to such process, method, system, or device. The term "a plurality of" involved in the present disclosure may mean two or more. "And/or" may describe a relationship between related objects, indicating that three relationships can exist, for example, "A and/or B" may indicate the following three cases: A exists alone, A and B exist simultaneously, and B exists alone. The terms "first", "second, "third", etc. involved in the present disclosure only distinguish similar objects and do not represent a specific ordering of the objects.

In the present disclosure, a patient refers to anyone who is undergoing or may undergo the detection of a Doppler blood flow detection device, and the patient may also be called as a sick person. A medical staff, for example, may include a person who uses the Doppler blood flow detection device to monitor a patient, and is therefore as one of users of the Doppler blood flow detection device. However, the user may not only include the medical staff, but may also include a person who directly or indirectly use the Doppler blood flow detection device.

Figure 1:
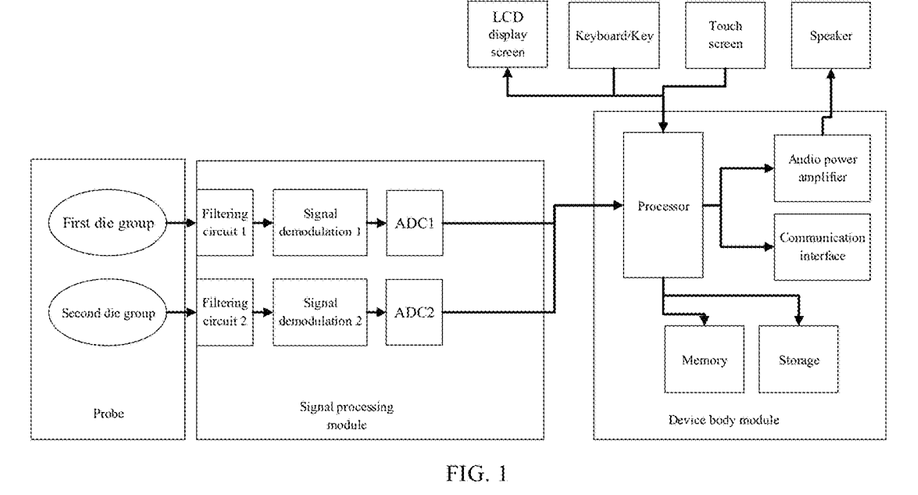
FIG. 1 is a structural block diagram illustrating a Doppler blood flow detection device according to an embodiment of the present disclosure.

An embodiment of the present disclosure provides a method for determining blood flow velocity using a dual die group, which may be applied to a Doppler blood flow detection device. Firstly, please refer to FIG. 1, which illustrates a Doppler blood flow detection device according to an embodiment of the present disclosure. As shown in FIG. 1, the Doppler blood flow detection device may include a probe, a signal processing module, and a device body module. Specifically, the probe may include a first die group and a second die group. The first die group and the second die group may be respectively connected to the signal processing module to transmit a detected signal to the signal processing module. The signal processing module may process the detected signal after receiving the detected signal transmitted from each die group. Specifically, the signal processing module may include a filtering circuit 1, a filtering circuit 2, a signal demodulation 1, a signal demodulation 2, an ADC 1, and an ADC 2. The first and second die groups may be connected to the filtering circuits 1 and 2 of the signal processing module, respectively. The filtering circuits 1 and 2 may perform filtering processing on the signals detected by the first and second die group dies, respectively. The filtering circuits 1 and 2 may be connected to the signal demodulation 1 and 2, respectively. The signal demodulation 1 and 2 may demodulate signals filtered by the filtering circuits 1 and 2, respectively. The signal demodulation 1 and 2 may be connected to the ADC 1 and ADC 2, respectively. The ADC 1 and ADC 2 may perform an analog-to-digital conversion process on signals demodulated by the signal demodulation 1 and the signal demodulation 2, respectively. The signal processed by the signal processing module may be transmitted to the processor. To store the received detection result, and intermediate quantities, and algorithm programs during an operation, the device also includes a storage module connected to the processor, such as a memory, a storage, etc. The device may also include a network port.

A communication interface may provide an interface for communication with other intelligent devices for transmitting data and achieving feedback. The communication interface may include a common communication hardware interface such as a USB/UART/network port/Bluetooth/WIFI/CAN, etc, which is not specifically limited in the present disclosure.

In addition, the device may also include an audio power amplifier and a speaker connected to the audio power amplifier. The speaker may be used for audio output of a result determined by the processor and audio output of information that needs to be reminded to a user.

In a specific example, the device may also include an input device. The input device may include but is not limited to at least one of a keyboard, a key, a voice control input device, and a touch screen. It can be understood that other devices capable of signal input can be included in the scope of the present disclosure. In addition, the device may also include an output device. The output device may include but is not limited to an LCD display screen. Certainly, other devices capable of signal output may be also included within the scope of the present disclosure. Thus, the device can realize information interaction with the user.

The method for determining the blood flow velocity using the dual die group according to the embodiment of the present disclosure can be applied to a Doppler blood flow detection device. The Doppler blood flow detection device includes a first die group and a second die group placed at different positions of a blood vessel to be detected. In an actual application, the first die group and the second die group may be jointly disposed within a probe. The Doppler blood flow detection device may be, for example, the Doppler blood flow detection device illustrated in FIG. 1.

Figure 2:
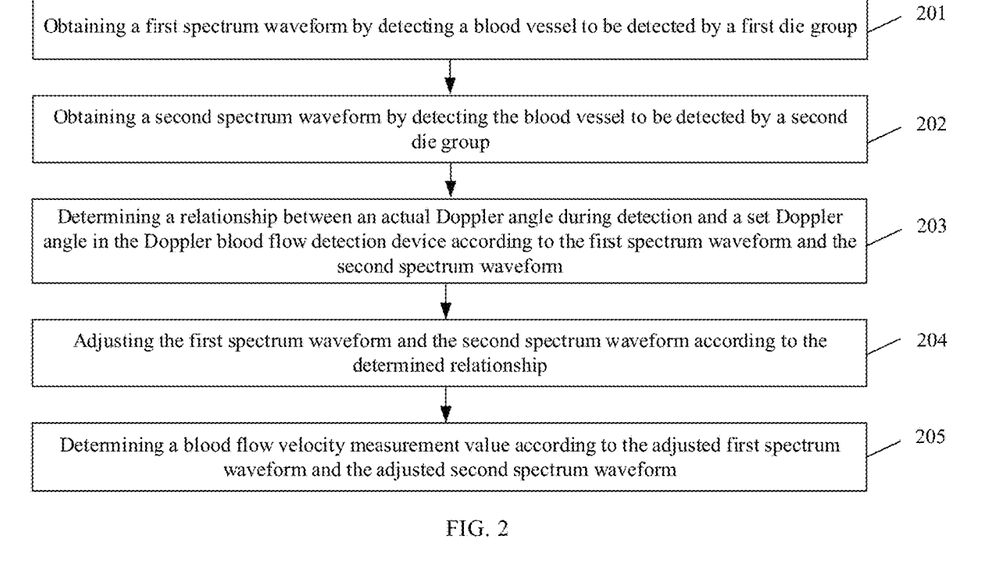
FIG. 2 is a schematic flowchart illustrating a method for determining blood flow velocity using a dual die group according to an embodiment of the present disclosure.

Please refer to FIG. 2, a method for determining blood flow velocity using a dual die group may include:

Step 201: obtaining a first spectrum waveform by detecting a blood vessel to be detected using a first die group;

Step 202: obtaining a second spectrum waveform by detecting the blood vessel to be detected using a second die group;

Step 203: determining a relationship between an actual Doppler angle during detection and a set Doppler angle in the Doppler blood flow detection device according to the first spectrum waveform and the second spectrum waveform;

Step 204: adjusting the first spectrum waveform and the second spectrum waveform according to the determined relationship; and Step 205: determining a blood flow velocity measurement value according to the adjusted first spectrum waveform and the adjusted second spectrum waveform.

Wherein, the first die group and the second die group are placed at different positions of the blood vessel to be detected. For example, one of the first die group and the second die group may be placed at a first position of the blood vessel to be detected, and the other one may be placed at a second position of the blood vessel to be detected. The first position and the second position are respectively a front position and a back position of the blood vessel to be detected along a blood flow direction, that is, the blood flow direction may be a direction from the first position to the second position. It should be understood that the blood vessel to be detected may be wrapped by the skin, and the first die group and the second die group may be obviously not in direct contact with the blood vessel to be detected. "The first die group and the second die group may be placed at different positions of the blood vessel to be detected" described herein may refer to that the first die group and the second die group may be placed across the skin at different positions corresponding to the blood vessel to be detected.

Figure 3:
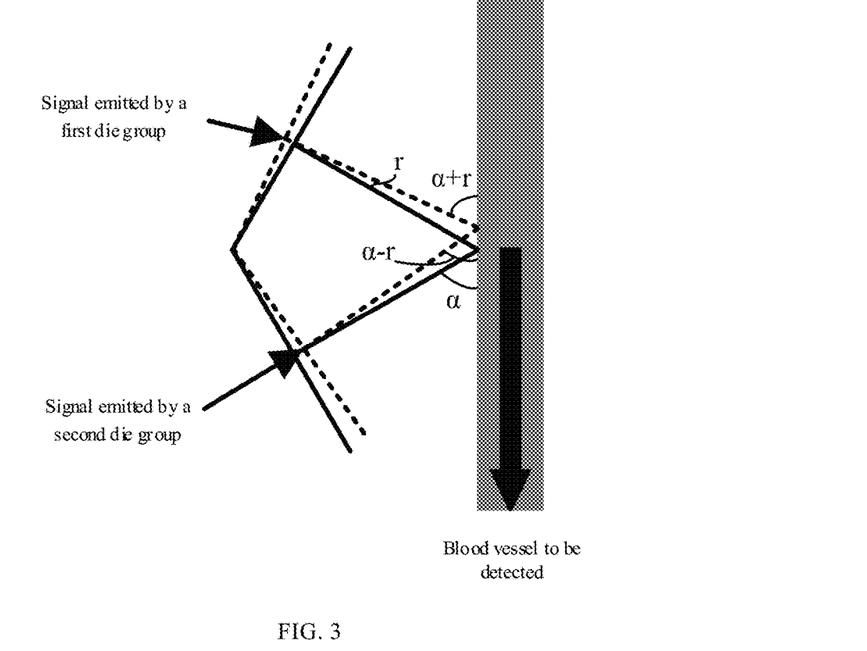
FIG. 3 is a schematic diagram illustrating a position of a Doppler blood flow detection device used to detect a blood vessel to be detected in a specific application.

The first spectrum waveform and the second spectrum waveform are obtained by detecting the blood vessel to be detected using the first die group and the second die group respectively, and the first die group and the second die group are placed at different positions of the blood vessel to be detected. FIG. 3 is a schematic diagram illustrating a position of the Doppler blood flow detection device used to detect the blood vessel to be detected in a specific application. The positon of the blood vessel and the position where the first die group and the second die group emit signals are briefly illustrated in FIG. 3. A solid line in FIG. 3 may represent a case that an actual Doppler angle during the detection may be consistant with a set Doppler angle in the Doppler blood flow detection device. That is, the actual Doppler angle may be equal to the set Doppler angle $\alpha$ (specifically an emitting angle, it is also referred to as an emitting angle $\alpha$ below) in the Doppler blood flow detection device. However, during an actual measurement, it is may be difficult to ensure that the actual Doppler angle is completely coincide with the set Doppler angle, which may cause a measurement error. A dotted line in FIG. 3 may represent a case that the actual Doppler angle may be not consistant with the set Doppler angle in the Doppler blood flow detection device. Assuming an deviation angle between the actual Doppler angle and $\alpha$ is r, at this time, for the first die group, the actual Doppler angle may be equal to $\alpha+r$, and for the second die group, the actual Doppler angle may be equal to $\alpha-r$. It can be understood that if only the first die group or the second die group is used, an obtained blood flow velocity measurement value V may be a vertical component of the actual blood flow velocity V0 in a direction of emitting or receiving a signal by a corresponding die group, and thus $V=V0/\cos\alpha$. Then, when the deviation angle r is 1°, the measurement error $\Delta V=V0/\cos\alpha-V0/\cos(\alpha\pm1)$. It can be seen that the larger the set Doppler angle is, the greater the measurement error is.

In order to reduce the error, the Doppler blood flow detection device applied in the embodiment of the present disclosure may include the above-mentioned first and second die groups. The collection of two Doppler channels is realized by the first die group and the second die group. Since the first die group and the second die group are placed at different positions of the blood vessel to be detected, two Doppler angles may be collected by the two Doppler channels, two sets of collected data may be respectively obtained according to the two Doppler angles, and two spectrum waveforms may be obtained according to the two sets of collected data. Please refer to FIG. 4, a channel receiving the collected data of the first die group may be referred to as "Channel 1", and a channel receiving the collected data of the second die group may be referred to as "Channel 2". The spectrum waveforms obtained through the channel 1 and the channel 2 are shown in (a) in FIG. 4.

The first die group may include at least one emitting die and at least one receiving die, and the second die group may also include at least one emitting die and at least one receiving die. The first die group and the second die group may emit and collect signals simultaneously. Measurement time corresponding to the first spectrum waveform and the second spectrum waveform may be the same.

Since the first spectrum waveform and the second spectrum waveform are obtained by measuring the same blood vessel to be detected at the same time, the difference between the first spectrum waveform and the second spectrum waveform may be caused by the difference between an actual Doppler angle of the first die group and an actual Doppler angle of the second die group. It can be understood that in an ideal status (i.e., the actual Doppler angle during the detection may be consistent with the set Doppler angle in the Doppler blood flow detection device), the actual Doppler angle during the detection of the first die group and the actual Doppler angle during the detection of the second die group may be the same, and are equal to the set Doppler angle. Thus, a relationship between the actual Doppler angle during the detection and the set Doppler angle in the Doppler blood flow detection device may be determined according to the first spectrum waveform and the second spectrum waveform.

As an alternative embodiment, determining the relationship between the actual Doppler angle during the detection and the set Doppler angle in the Doppler blood flow detection device according to the first spectrum waveform and the second spectrum waveform may include: determining a first peak value according to the first spectrum waveform; determining a second peak value according to the second spectrum waveform; and determining that the actual Doppler angle during the detection and the set Doppler angle based on the first peak value and the second peak value satisfy the following relationship: $\cos(\alpha+r)/\cos(\alpha-r)=Vm1/Vm2$, where, Vm1 may represent the first peak value, Vm2 may represent the second peak value, α may represent the set Doppler angle, r may represent the deviation angle between the actual Doppler angle during the detection and α, and α+r and α−r may represent the actual Doppler angles during the detection of the first die group and the second die group, respectively.

Further, the step of determining the first peak value according to the first spectrum waveform and/or the step of determining the second peak value according to the second spectrum waveform may include determining a plurality of peak values in a plurality of cycles according to the spectrum waveform; eliminating an abnormal value from the plurality of peak values using the Pauta criterion; and calculating an average value of peak values remained after eliminating the abnormal value.

It is easy to understand that if the step of determining the first peak value according to the first spectrum waveform includes determining the plurality of peak values in the plurality of cycles according to the first spectrum waveform and eliminating the abnormal value using the Pauta criterion, a first average value may be obtained by calculating the average value of the peak values remained after eliminating the abnormal value, and the first average value may be determined as the first peak value. Similarly, if the step of determining the second peak value according to the second spectrum waveform includes determining the plurality of peak values in the plurality of cycles according to the second spectrum waveform and eliminating the abnormal value from the plurality of peak values using the Pauta criterion, a second average value may be obtained by calculating the average value of the peak values remained after eliminating the abnormal value, and the second average value may be determined as the second peak value.

Figure 4:
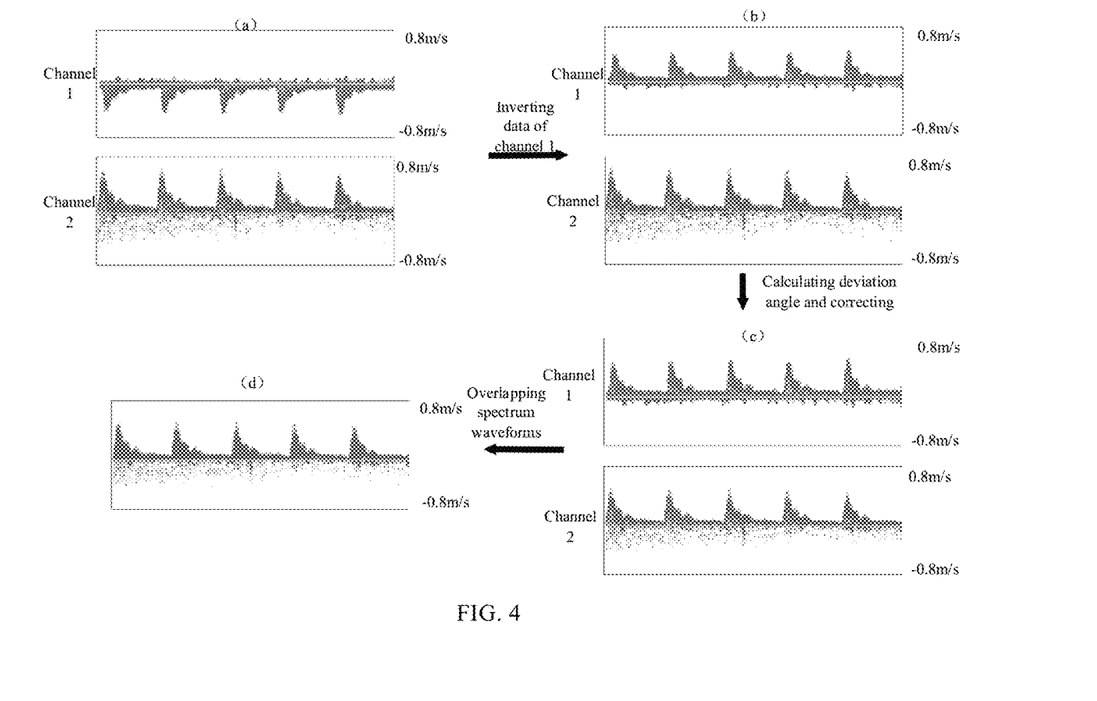
FIG. 4 is a flow chart of processing a spectrum waveform in a specific application.

Please continue to refer to FIG. 4, in a specific application, the first spectrum waveform may be inverted. Inverted data of channel 1 is illustrated in (b) of FIG. 4.

To more accurately determine the peak value of each spectrum waveform, five cycles may be selected, a peak value of each cycle in the selected five cycles may be calculated, and five peak values may be obtained. Then, an abnormal value may be eliminated from the five peak values using the Pauta criterion. Certainly, this step only means that the operation of eliminating the abnormal value using the Pauta criterion may be performed, and does not mean that there must be an abnormal value to be eliminated. In other words, if the five peak values have no abnormal values, all of the five peak values will be retained. Then, an average value of the peak values remained after eliminating the abnormal value is calculated. Certainly, this step only means that the operation of calculating the average value is performed, if only one peak value is remained after eliminating the abnormal value, and the average value is the peak value.

Further, the above steps may be performed for the first spectrum waveform and the second spectrum waveform to obtain average values respectively, and the average values may be correspondingly determined as the first peak value Vm1 and the second peak value Vm2.

Then, r may be calculated according to an Equation: $\cos(\alpha+r)/\cos(\alpha-r)=Vm1/Vm2$. r may represent the deviation angle between the actual Doppler angle during the detection and α, which can also be referred to as a tilt angle for short. Further, data of channel 1 and channel 2 may be accordingly adjusted according to r, and this step can also be called as correction.

Specifically, adjusting the first spectrum waveform and the second spectrum waveform according to the determined relationship may include adjusting the first spectrum waveform and the second spectrum waveform according to the following Equations: $Vm1'=Vm1*\cos \alpha/\cos(\alpha+r)$, $Vm2'=Vm2*\cos \alpha/\cos(\alpha-r)$, where Vm1 represents the first peak value, Vm2 represents the second peak value, Vm1' represents a peak value corresponding to the adjusted first spectrum waveform, Vm2' represents a peak value corresponding to the adjusted second spectrum waveform, α represents the set Doppler angle, r represents the deviation angle between the actual Doppler angle during the detection and α, and α+r and α−r represent the actual Doppler angles during the detection of the first die group and the second die group, respectively.

In an actual operation, specifically, the first spectrum waveform and the second spectrum waveform may be scaled in corresponding proportions according to the determined relationship to obtain the corrected spectrum waveforms. Please refer to (c) in FIG. 4, the two corrected spectrum waveforms may be highly similar.

As an alternative implementation, determining the blood flow velocity measurement value according to the adjusted first spectrum waveform and the adjusted second spectrum waveform may include obtaining an overlapped spectrum waveform by overlapping the adjusted first spectrum waveform and the adjusted second spectrum waveform; and determining the blood flow velocity measurement value according to the overlapped spectrum waveform.

The overlapped spectrum waveform can be referred to (d) in FIG. 4. The overlapped spectrum waveform may further integrate a detection result of the first die group with a detection result of the second die group, thereby neutralizing the angle errors between them. Determining the blood flow velocity measurement value according to the overlapped spectrum waveform may be performed using existing technical means in the field, which is not specifically limited in the present disclosure.

It can be understood that the blood flow velocity measurement value in this way may be closer to the actual blood flow velocity, and the error caused by the inconsistency between the angle between the probe in the actual measurement and the blood vessel to be detected and the set Doppler angle may be basically eliminated, thereby improving the accuracy of the blood flow velocity measurement value.

In a specific application, a frequency of a signal emitted by an emitting die in the first die group and a frequency of a signal emitted by an emitting die in the second die group may be different. Thus, the Doppler blood flow detection device may include a dual frequency dual channel abnormality probe detection device.

Alternatively, the frequency of the signal emitted by the first die group and the frequency of the signal emitted by the second die group are in the range of 1 MHz-16 MHz to meet the requirements of dual frequency dual channel detection. Further, the frequency of the signal emitted by the first die group and the frequency of the signal emitted by the second die group are in the range of 2 MHz-8 MHz, and the accuracy of the detection result can be better.

To improve the accuracy of the detection result, the frequency F1 of the signal emitted by the first die group and the frequency F2 of the signal emitted by the second die group may satisfy the following relationships: 1. F1<F2, 2. the remainder of F2 taking F1 is greater than 0.5 MHz, and 3. F2<3F1.

Wherein, the remainder of F2 taking the of F1 is greater than 0.5 MHz may also be expressed as F2% F1>0.5 MHz.

Taking the remainder is to take out an extra part that is not divisible. Specifically, if F2=nF1+x, where n represents a positive integer and x<F1, the remainder of F2 taking F1 is equal to x.

As a preferred example, F1=2.1 MHz-2.7 MHz, and F2=3.8 MHz-4.3 MHz.

In a specific example, a notch filter may be used in the signal filtering of the first die group and the second die group, and a bandwidth of one of them may be in a range of F1-0.5 MHz~F1+0.5 MHz, and a bandwidth of the other one may be in a range of F2-0.5 MHz~F2+0.5 MHz. In such a way, different channels may be set with different filter bandwidths. When dual channels simultaneously emit signals, the receiving dies on both sides may receive the signals of the two emitting dies, and an interference may occur with each other. In this specific example, the filter of the corresponding frequency band of the corresponding channel may be selected, and thus the signal of the other channel may be suppressed, thereby achieving a better signal-to-noise ratio.

Ultrasonic interference in the dual channels may be removed through filtering and demodulation techniques.

It can be understood that the first die group and the second die group may be disposed in the probe of the Doppler blood flow detection device, and may be disposed in a same probe. However, it should be noted that the embodiment of the present disclosure does not exclude the situation that the first die group and the second die group are respectively disposed in two probes. If the first die group and the second die group are respectively disposed in two probes, there is a mechanical connection relationship between the two probes, so that positions of the two probes may be correlated to ensure that when a deviation angle occurs, the deviation angles of the first die group and the second die group may be ±r, respectively.

As an alternative implementation, the method may further include: determining a roll angle of the probe in a detection state, wherein the roll angle may be an angle formed between a projection direction of a sound field emitted by an emitting die in the probe on a horizontal plane and a blood flow direction in the blood vessel to be detected, and the emitting die may be an emitting die in the first die group and/or the second die group; and correcting the blood flow velocity measurement value according to the roll angle to obtain a corrected blood flow velocity measurement value.

In a specific application, the Doppler blood flow detection device may also include an attitude sensor disposed in the probe (not shown in FIG. 1), and determining the roll angle of the probe in the detection state may include: determining the roll angle of the probe in the detection state using the attitude sensor.

The attitude sensor may be a high-performance three-dimensional motion attitude measurement instrument. The attitude sensor may include at least one of the following motion sensors: a three-axis acceleration sensor, a gyroscope, and a three-axis electronic compass, etc.

As an alternative implementation, the attitude sensor may include the three-axis acceleration sensor, and determining the roll angle of the probe in the detection state may include: obtaining acceleration components of the gravity acceleration in directions of three mutually perpendicular coordinate axes in the detection state based on the three-axis acceleration sensor, and determining the roll angle according to the acceleration components.

In a specific application, when starting to measure the blood flow velocity, the user may place the probe at a measurement position according to a predetermined usage manner. The predetermined usage manner may be, for example, to ensure that the projection direction of the sound field emitted by the emitting die in the probe on the horizontal plane may be perpendicular to the blood flow direction in the blood vessel to be detected, and do not produce a discrete angle, thereby reducing the measurement error. During the measurement process, the patient can be considered to be stationary. At this time, an initial output value of the three-axis acceleration sensor can be recorded as a reference for a subsequent calculated roll angle.

It can be understood that, taking the blood vessel to be detected located in the horizontal plane as an example, if a chip of the three-axis acceleration sensor is placed horizontally, and a rectangular coordinate system including three coordinate axes of XYZ is established in the direction of the three-axis acceleration sensor, components of the gravity acceleration g in the X-axis and Y-axis directions are both 0, and the component in the Z-axis direction is g.

In an actual measurement, especially during a long-term monitor, it is likely that due to a movement of the patient, the projection direction of the sound field emitted by the emitting die in the probe on the horizontal plane may be not perpendicular to the blood flow direction in the blood vessel to be detected, and thus the measurement error may be caused.

Figure 5:
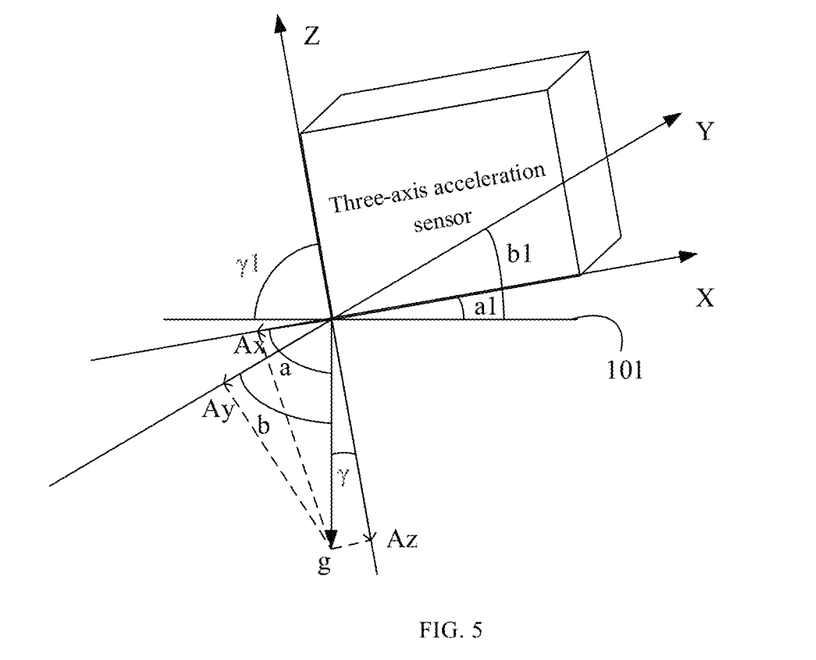
FIG. 5 is a schematic diagram illustrating a position relationship between a three-axis acceleration sensor and a blood vessel to be detected when a roll angle is not equal to 90°.

FIG. 5 illustrates a position relationship between a three-axis acceleration sensor and a blood vessel to be detected when a roll angle is not equal to 90°. Since the three-axis acceleration sensor is located in a probe, FIG. 5 also illustrates a position relationship between the three-axis acceleration sensor and the blood vessel to be detected when the projection direction of a sound field emitted by an emitting die in the probe on a horizontal plane is not perpendicular to a blood flow direction in the blood vessel to be detected. As shown in FIG. 5, a component of the gravity acceleration g in an X-axis direction is Ax, an angle between Ax and a blood vessel 101 to be detected is a1, and an angle between Ax and the gravity acceleration g is a; the component of the gravity acceleration g in a Y-axis direction is Ay, an angle between Ay and the blood vessel 101 to be detected is b1, and an angle between Ay and the gravity acceleration g is b; the component of the gravity acceleration g in a Z-axis direction is Az, an angle between Az and the blood vessel 101 to be detected is γ1, and an angle between Az and the gravity acceleration g is γ. The relationship between the angles is: a=90°−a1, b=90°−b1, and γ=90°−γ1.

Components of the gravity acceleration g in each axis direction are: Ax=g cos a, Ay=g cos b, Az=g cos γ; or: Ax=g sin a1, Ay=g sin b1, Az=g sin γ1.

Further:

$$g*g = Ax*Ax + g\cos a1 * g\cos a1;$$

$$g\cos a1 = squr\ (g*g - Ax*Ax);$$

Similarly, $$g\cos b1 = squr\ (g*g - Ay*Ay);$$

$$g\cos \gamma 1 = squr\ (g*g - Az*Az).$$

In solid geometry, g may be equivalent to a diagonal of a cube, and Ax, Ay, and Az may be equivalent to three sides, and according to the Pythagorean theorem: Ax*Ax+Ay*Ay+Az*Az=g*g.

Taking the X axis as an example, sin a1=Ax/g, cos a=squr(g*g−Ax*Ax)/g;

$$\tan a1 = Ax/squr\ (g*g - Ax*Ax) = Ax/squr\ (Ay*Ay + Az*Az).$$

Similarly, $$\tan b1 = Ay/squr\ (Ax*Ax + Az*Az);$$

$$\tan \gamma1 = Az/squr\ (Ax*Ax + Ay*Ay).$$

Thus, relationships between the measurement value of the three-axis acceleration sensor and a1, b1, and γ1 are obtained. Here, values of a1, b1, and γ1 may be equal to corresponding radian values.

Next, a radian value between each axis and the horizontal line (refer to the blood vessel 101 to be detected in FIG. 5) may be calculated. Here, a11, b11, and γ11 may represent a radian value between the X-axis direction and the horizontal line, a radian value between the Y-axis direction and the horizontal line, and a radian value between the Z-axis direction and the horizontal line, respectively.

$$a11 = \arctan(Ax/squr\ (Ay*Ay + Az*Az)),$$

$$b11 = \arctan(Ay/squr\ (Ax*Ax + Az*Az)),\ \text{and}$$

$$\gamma11 = \arctan(Az/squr\ (Ax*Ax + Ay*Ay)).$$

Next, the calculation is performed using the following Equation: radian value=angle value*πR/180, that is, angle value=radian value*180/πR, where R is 1. The angle value of each axis may be obtained:

$$\phi = a11 * 180/\pi = [\arctan(Ax/squr(Ay*Ay + Az*Az))] * 180/\pi,$$

$$\psi = b11 * 180/\pi = [\arctan(Ay/squr(Ax*Ax + Az*Az))] * 180/\pi,$$

and $$\theta = \gamma11 * 180/\pi = [\arctan(Az/squr(Ax*Ax + Ay*Ay))] * 180/\pi.$$

where, ψ represents the angle value corresponding to the radian value b11, θ represents the angle value corresponding to the radian value γ 11, φ represents the angle value corresponding to the radian value a11, and φ represents the roll angle.

It can be understood that the directions of the three coordinate axes which are mutually perpendicular to each other may be established according to the direction of the three-axis acceleration sensor in the measurement state. The three-axis acceleration sensor and the emitting die may be disposed in the probe together. Thus, the direction of the three-axis acceleration sensor may represent the direction of the emitting die, and the angle between the projection direction of the sound field emitted by the emitting die on the horizontal plane and the blood flow direction can be determined according to the components of the acceleration.

In another alternative implementation, the attitude sensor may include a gyroscope, and determining the roll angle of the probe in the detection state may include: obtaining the roll angle in the detection state based on the gyroscope.

Figure 6:
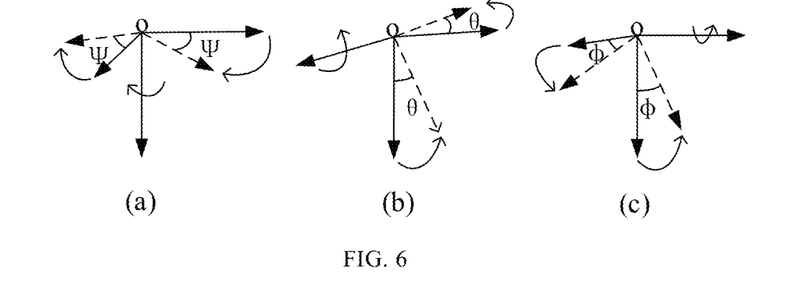
FIG. 6 is a schematic diagram illustrating a yaw angle, a pitch angle, and a roll angle.

FIG. 6 is a schematic diagram illustrating a yaw angle, a pitch angle, and a roll angle, wherein (a) shows the yaw angle ψ, (b) shows the pitch angle θ, and (c) shows the roll angle φ. A spatial trajectory of a moving object may be decomposed into independent motions along Z, Y, and X axes. A component of a motion vector in each axis may be represented by the cosine of an angle between the vector and each axis. The moving object may be, for example, an attitude sensor. There are nine parameters in the direction cosine, which may be represented by a third-order direction cosine matrix $C_b^n$. Components of the $C_b^n$ may be as follows:

$$C_b^n = \begin{bmatrix} c_{11} & c_{12} & c_{13} \\ c_{21} & c_{22} & c_{23} \\ c_{31} & c_{32} & c_{33} \end{bmatrix}.$$

A third-order Euler rotation of the moving object may be expressed by cosine matrices in Three-directions:

$$C_z(\psi) = \begin{bmatrix} \cos\psi & \sin\psi & 0 \\ -\sin\psi & \cos\psi & 0 \\ 0 & 0 & 1 \end{bmatrix},$$

$$C_y(\theta) = \begin{bmatrix} \cos\theta & 0 & -\sin\theta \\ 0 & 1 & 0 \\ \sin\theta & 0 & \cos\theta \end{bmatrix},$$

and $$C_x(\phi) = \begin{bmatrix} 1 & 0 & 0 \\ 0 & \cos\phi & \sin\phi \\ 0 & -\sin\phi & \cos\phi \end{bmatrix}.$$

A product of cosine matrices $C_n^b$ may be used to represent a transformation from a geographical coordinate system to a coordinate system of the moving object:

$$C_n^b = C_\phi C_\theta C_\psi,\ C_n^b = \begin{bmatrix} \cos\theta\cos\psi & \cos\theta\sin\psi & -\sin\theta \\ \sin\phi\sin\theta\cos\psi - & \sin\phi\sin\theta\sin\psi + & \sin\phi\cos\theta \\ \cos\phi\sin\psi & \cos\phi\cos\psi & \\ \cos\phi\sin\theta\cos\psi + & \cos\phi\sin\theta\sin\psi - & \cos\phi\cos\theta \\ \sin\phi\sin\psi & \sin\phi\cos\psi & \end{bmatrix},$$

$$C_b^n = \begin{bmatrix} \cos\theta\cos\psi & \sin\phi\sin\theta\cos\psi - & \cos\phi\sin\theta\cos\psi + \\ & \cos\phi\sin\psi & \sin\phi\sin\psi \\ \cos\theta\sin\psi & \sin\phi\sin\theta\sin\psi + & \cos\phi\sin\theta\sin\psi - \\ & \cos\phi\cos\psi & \sin\phi\cos\psi \\ -\sin\theta & \sin\phi\cos\theta & \cos\phi\cos\theta \end{bmatrix}.$$

After obtaining an attitude update matrix $C_b^n$ of the coordinate system of the moving object relative to the geographical coordinate system, an angular rate data obtained by the attitude sensor may be converted into attitude angle data.

$$[A_x^a A_y^a A_z^a] = [0\ 0\ 1]C_b^n,$$

$A_x^a$, $A_y^a$, $A_z^a$ represent components of the gravity measured by an accelerometer in each axis direction, and [0 0 1] represents components of the gravity field measured by the accelerometer in each axis in the geographical coordinate system.

A tilt angle (the roll angle φ and the pitch angle $\theta$) may be obtained using the inverse trigonometric function:

$$\theta = \sin^{-1}(-A_x^a),$$

$$\phi = \sin^{-1}\left(\frac{A_y^a}{\cos\theta}\right).$$

In actual use, according to the characteristics of the human body, it could be considered that the relative angle between the Z-axis direction and the direction of the blood vessel to be detected may be not changed, that is, γ and γ1 may remain unchanged, that is, the pitch angle may remain unchanged, and the angle correction may be performed using the roll angle φ.

It can be understood that when the human body changes a position, the positions of the attitude sensor and the blood vessel to be detected may be changed synchronously. In the Doppler effect, what matters is an angle parallel to a plane in which the blood flow direction of the blood to be detected is located.

In this embodiment, the blood flow velocity measurement value may be determined according to the adjusted first spectrum waveform and the adjusted second spectrum waveform. The blood flow velocity measurement value may be corrected to obtain the corrected blood flow velocity measurement value. Specifically, the following Equation may be used for the correction: V1=V/sin φ, where V1 represents the corrected blood flow velocity measurement value, V represents the blood flow velocity measurement value before correction, and φ represents the roll angle.

Figure 7:
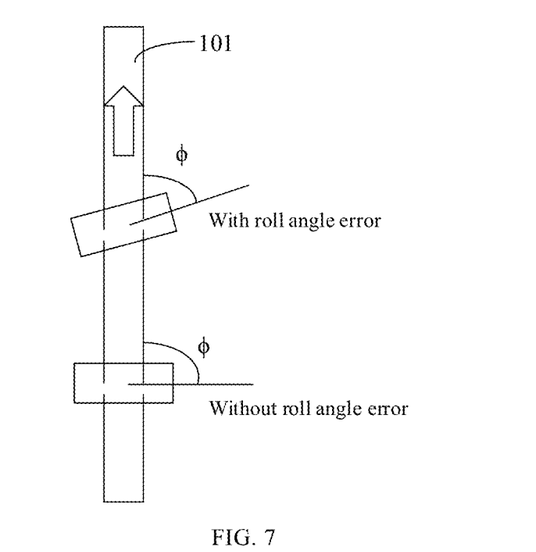
FIG. 7 is a schematic diagram illustrating a position where a blood vessel to be detected is detected in a condition that there is a roll angle error and in a condition that there is no roll angle error.

Please refer to FIG. 7, when a probe is placed in a measurement position according to a predetermined usage manner, the roll angle φ may be equal to 90°. At this time, there is no roll angle error in the measurement result. When the roll angle error exists, that is, after the probe rotates, according to the principle of a velocity component, the blood flow velocity measurement value obtained at this time may be the velocity component of the blood flow velocity measurement value in a direction after the rotation that should be obtained without the roll angle error. Thus, the corrected blood flow velocity may be obtained according to the Equation: V1=V/sin φ, which is or theoretically equal to the corrected blood flow velocity measurement value that should be obtained without the roll angle error.

It can be understood that when the roll angle φ is equal to 90°, V1=V may be obtained according to the above Equation V1=V/sin φ, which may further indicate that there is no roll angle error in the measurement result.

In the embodiment, the blood flow velocity measurement value determined in step 205 may be corrected, thereby further improving the accuracy of the blood flow velocity measurement value to be output. Optionally, the corrected blood flow velocity measurement value may be output as an output value.

As an alternative implementation, step 201 and/or step 202 may include: obtaining an emitting angle that is an angle between a direction of emitting a signal by the emitting die in the first die group and/or the second die group and a blood flow direction in the blood vessel to be detected; obtaining a distance between the emitting die and a receiving die disposed in a same die group in the Doppler blood flow detection device and a distance between the emitting die and the blood vessel to be detected; determining a receiving angle according to the emitting angle, the distance between the emitting die and the receiving die, and the distance between the emitting die and the blood vessel to be detected, wherein the receiving angle is an angle between a direction in which the signal is received by the receiving die of the first die group and/or the second die group and the blood flow direction; and determining the first spectrum waveform and/or the second spectrum waveform according to the emitting angle and the receiving angle.

In this way, the receiving angle may be determined according to the emitting angle, the distance between the emitting die and the receiving die, and the distance between the emitting die and the blood vessel to be detected, and a spectrum waveform may be determined according to the emitting angle and the receiving angle, thereby obtaining a more accurate spectrum waveform. Especially when the blood vessel to be detected is a superficial blood vessel, such as a human carotid artery, etc., it can obtain a result that is closer to the real occasion by this implementation.

Wherein, obtaining the emitting angle may specifically include: obtaining the emitting angle α pre-stored in the Doppler blood flow detection device (i.e., the set Doppler angle). It can be understood that a specific value of the emitting angle α may be a fixed angle value determined during the design of the Doppler blood flow detection device.

Obtaining a distance D between an emitting die T and a receiving die R disposed in a same die group in the Doppler blood flow detection device may specifically include: obtaining a pre-stored distance D between the emitting die T and the receiving die R disposed in the same die group in the Doppler blood flow detection device. The distance D may be a fixed value determined during the design of the Doppler blood flow detection device.

Figure 8:
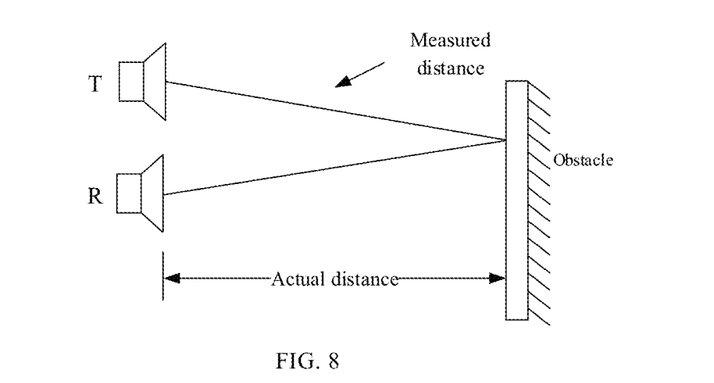
FIG. 8 is a schematic diagram illustrating the principle of determining a first distance using an ultrasonic wave according to a specific example of the present disclosure.

A distance between the emitting die T and a blood vessel 101 to be detected may include a first distance L, and the first distance L may be a distance from the emitting die T to the blood vessel 101 to be detected along a direction in which the emitting die T emits a signal. The receiving angle β may be determined according to the emitting angle α, the distance D between the emitting die T and the receiving die R, and the distance L between the emitting die T and the blood vessel 101 to be detected, which may include determining the receiving angle β according to the following Equation: |β−α|=arctan (D/L), where, β represents the receiving angle, α represents the emitting angle, |β−α| represents an absolute value of a difference between the receiving angle and the emitting angle, D represents the distance between the emitting die and the receiving die, and L represents the first distance.

Please refer to FIG. 8, exemplarily, obtaining the distance between the emitting die T and the blood vessel 101 to be detected may include: obtaining a duration t from die emitting the signal by the emitting die T to receiving the signal by the receiving die R; determining a propagation distance of the signal in the duration t according to the duration t and a propagation speed c of the signal; and determining the first distance L according to the propagation distance.

In a practical application, obtaining the distance between the emitting die T and the blood vessel 101 to be detected may be achieved by measuring using A-ultrasound, B-ultrasound, and other technologies. Please continue to refer to FIG. 8, the transmitter T may be, for example, an ultrasonic transmitter, the receiver R may be, for example, an ultrasonic receiver, and an obstacle may be, for example, a blood vessel to be detected. The transmitter T may emit a short section of an ultrasonic wave with a fixed-frequency to the obstacle, and the timing starts when the transmitter T starts to emit the ultrasonic wave. The ultrasonic wave may propagate in the object with the propagation speed c and time. After being reflected by the obstacle, the ultrasonic wave may enter the receiver R. A duration from the emission to the reception may be measured as t, the propagation speed of the ultrasonic wave in the object is c, and the measured distance can be calculated, and an actual distance may be estimated according to the measured distance. The first distance may be determined according to the following Equation: $L=c*t/2$.

Specifically, a combination of an original collection circuit and a sensor may be used to collect Doppler by applying a PW pulse wave Doppler, and a time difference between the emission to the reception may be recorded in each generation cycle to calculate the measured distance and an angle. This method may use time domain data for analytical calculations.

Since the propagation speed of the ultrasonic wave in human tissue is $c=1570$ m/s$=1570000$ mm/s, a depth of a blood vessel in the neck is between 5 mm and 30 mm (that is, H is between 5 mm and 30 mm), and a range of L is between 7 mm and 42 mm. The range of T is between $7/1570000\sim42/1570000$s, $7/1570\sim42/1570$ ms, or 4.5 μs~27 μs. A frequency of the used ultrasonic wave may be between 2 MHz and 8 MHz. Specifically, the frequency of the ultrasonic wave may be 4 MHz. Taking the frequency of the ultrasonic wave of 4 MHz as an example, the duration of each transmission cycle is ¼ MHz=0.25 μs, and after transmitting ultrasonic waves of 5 cycles, the total transmission duration is 1.25 s, which can meet a collection interval.

Figure 9:
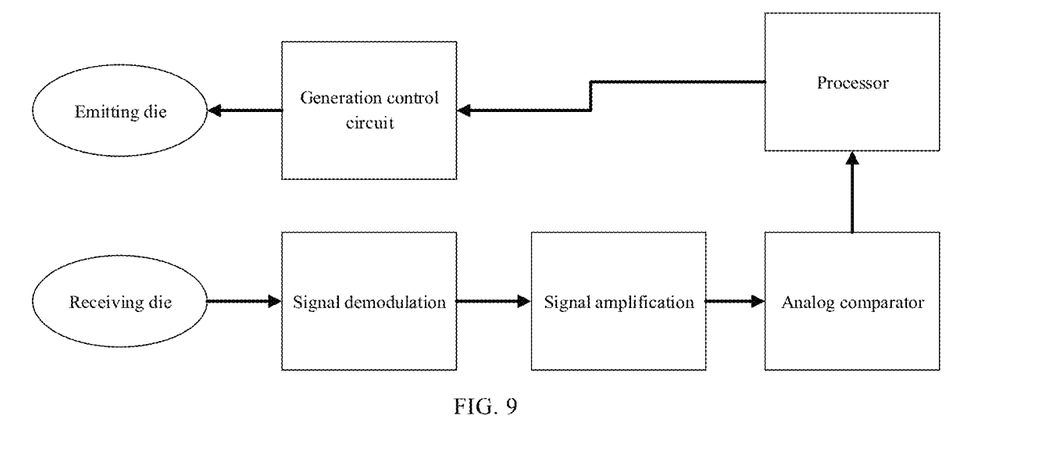
FIG. 9 is a block diagram illustrating a circuit for using an ultrasonic wave to determine a first distance according to a specific example of the present disclosure.
Figure 10:
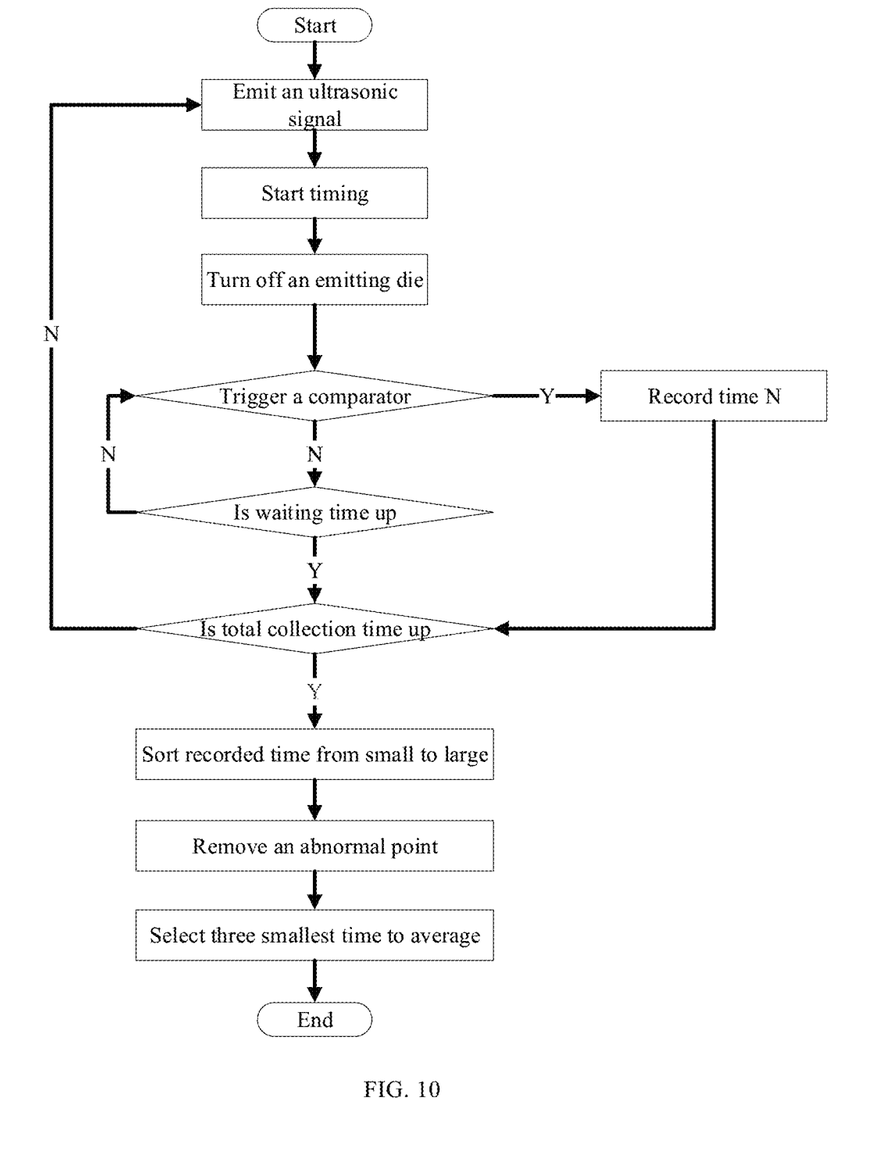
FIG. 10 is a schematic flowchart of determining a first distance using an ultrasonic wave according to a specific example of the present disclosure.

FIG. 9 is a block diagram illustrating a circuit for using an ultrasonic wave to determine a first distance according to a specific example of the present disclosure. FIG. 10 is a schematic flow chart illustrating using an ultrasonic wave to determine a first distance according to a specific example of the present disclosure.

Firstly, please refer to FIG. 9, the circuit in FIG. 9 may be a part of a signal conditioning part in an overall circuit and specially used for measuring a distance. Wherein, a generation control circuit, a signal demodulation, and a signal amplification may be shared. When performing a distance measurement, the generation control circuit may control an emitting die to emit a signal. After a receiving die receives the signal, the signal may be demodulated and amplified by the signal demodulation and the signal amplification, respectively. The received signal may be input to an ADC (not shown in FIG. 9). When performing the distance measurement, the signal may be input into an analog comparator for comparison. An output of the analog comparator may be a digital signal, which may be directly collected by an I/O pin of a processor.

Subsequently, please refer to FIG. 10, determining the first distance using the ultrasonic wave may include: after starting the distance measurement, the emitting die may emit an ultrasonic signal, and the timing may start, and the emitting die may be turned off, the ultrasonic signal may be transmitted through the tissue to the blood and collide with the blood, and reflected to the receiving die after the Doppler effect occurs. The receiving die may perform i/q demodulation on the ultrasonic signal. The demodulated signal may be output as a weak analog signal, and the signal amplifier circuit may amplify the signal to a set range. When the blood flow velocity is greater, the signal may be greater. A comparison voltage V0 may be set, when the signal is greater than V0, the analog comparator may output 1, and when the signal is less than V0, the analog comparator may output 0.

Determining each cycle of measuring the distance may include: the emitting die starts to emit the ultrasonic signal and the timing starts die, if the output of the analog comparator changes from 0 to 1, it may be considered the ultrasonic transmission time measured in this cycle may be obtained. Specifically, judging whether the result of the comparator is yes or no. If the result is yes, the time N is recorded, and if the result is no, waiting time is up till total collection time is up.

Since in a pulsation cycle, the velocity of a dynamic blood flow is from small to large and then back to small, in a design circuit, the larger the blood flow velocity is, the larger the signal is, and the earlier the analog comparator is triggered. In this case, the measured time is more accurate. Therefore, optionally, set a time period, such as the measured time of 2 s-5 s, preferably 3 s, to ensure that the signal in the maximum blood flow state can be measured in one measured time. In the case of 3 s, the measured patient's pulse may be 20 bpm, which can meet the clinical requirement.

As shown in FIG. 10, from the ultrasonic wave is emitted to the total collection time is up, recorded time may be sorted from small to large, an abnormal point may be removed, three smallest time may be selected to be averaged, and the distance measurement may be ended.

The first distance may be determined according to the Equation $L=c*t/2$, and a receiving angle may be determined according to the Equation: $|\beta-\alpha|=\arctan(D/L)$.

As another alternative implementation, obtaining the distance between the emitting die T and the blood vessel 101 to be detected may include: obtaining a second distance H input by an user via an input device, the second distance H is a distance between the emitting die T and the blood vessel 101 to be detected in a direction perpendicular to a skin surface; determining the first distance L according to the second distance H, wherein the first distance L is determined according to the following Equation: $L=H/\sin\alpha$, where, H represents the second distance.

Wherein, the second distance H may be input into the Doppler blood flow detection device by, for example, a medical staff.

Figure 11:
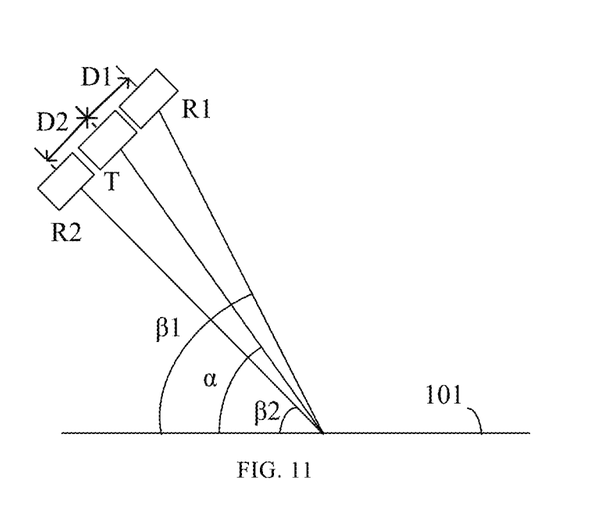
FIG. 11 is a schematic diagram of a position where a first die group and/or a second die group including a first receiving die and a second receiving die detects a blood vessel to be detected according to a specific example of the present disclosure.

Please refer to FIG. 11, optionally, a receiving die disposed in a first die group and/or a second die group may include a first receiving die R1 and a second receiving die R2. The first receiving die R1 and the second receiving die R2 may receive a signal emitted by a same emitting die T. A distance D1 between the emitting die T and the first receiving die R1 may be the same as a distance D2 between the emitting die T and the second receiving die R2. Determining a receiving angle according to an emitting angle, a distance between the emitting die and the receiving die, and a distance between the emitting die and a blood vessel to be detected may include: determining a first receiving angle β1 and a second receiving angle β2, wherein the first receiving angle β1 is an angle between a direction in which the first receiving die R1 receives the signal and a direction of the blood flow, and the second receiving angle β2 is an angle between a direction in which the second receiving die R2 receives the signal and the direction of the blood flow. Determining a blood flow velocity measurement value according to the emitting angle and the receiving angle may include: determining a first blood flow velocity measurement value V10 according to the emitting angle α and the first receiving angle β1, determining a second blood flow velocity measurement value V20 according to the emitting angle α and the second receiving angle β2, and determining the blood flow velocity measurement value V according to the first blood flow velocity measurement value V10 and the second blood flow velocity measurement value V20.

Wherein, the distance D1 between the emitting die T and the first receiving die R1 may be the same as the distance D2 between the emitting die T and the second receiving die R2, so α−β2≈β1−α, and assuming the angle difference is F. When the emitting die T emits a signal, the first receiving die R1 and the second receiving die R2 can receive the signal at the same time. A velocity component corresponding to the first receiving element R1 may be equal to a velocity component corresponding to the second receiving element R2, Δf1=Δf2=Δf*cos ε.

Assuming $$\alpha = 60°,$$

when $$\varepsilon = 9.823°,$$

$$\beta 1 = \alpha + \varepsilon = 69.823°,$$

and $$\beta 2 = \alpha - \varepsilon = 50.177°\circ$$

Assuming $$\Delta f * c / 2f = A,$$

If the difference between the emitting angle and the receiving angle is not considered, the actual blood flow velocity that should be detected is V11=Δf*c/(2f*cos α)=A/cos α=A/0.5=2A.

In this method, the blood flow velocity measurement value V may be determined according to the first blood flow velocity measurement value V10 and the second blood flow velocity measurement value V20. Specifically, for example, an average value of the first blood flow velocity measurement value V10 and the second blood flow velocity measurement value V20 is determined as the blood flow velocity measurement value V. Thus, $$V10 = \Delta f * c / (f * (\cos\alpha + \cos\beta 1)) = 2A / (\cos 60° + \cos 69.823°) = 2.332A,$$

$$V20 = \Delta f * c / (f * (\cos\alpha + \cos\beta 2)) = 2A / (\cos 60° + \cos 50.177°) = 1.748A,$$

and $$V = (V1 + V2)/2 = 2.04A.$$

In this way, it can reduce the error by this method, and the smaller R is, the smaller the error is.

On this basis, an embodiment of the present disclosure may also provide a Doppler blood flow detection device, which is used to implement the method for determining the blood flow velocity using the dual-die group in any one of the above embodiments.

It should be understood that detailed technical features of the Doppler blood flow detection device can refer to the relevant descriptions in the above embodiments of the method for determining blood flow velocity using the dual die group, and will not be repeated again herein.

It should be understood that although the steps in each flow chart of the present disclosure are shown in sequence as indicated by the arrows, these steps are not necessarily executed in the order indicated by the arrows. Unless explicitly stated in this disclosure, there is no strict order restriction on the execution of these steps, and these steps can be executed in other orders. Moreover, at least some of the steps in the drawings may include a plurality of steps or stages. These steps or stages may be not necessarily executed at the same time, but may be executed at different time. The execution order of these steps or stages may be not necessarily performed sequentially, and may be performed in turn or alternately with other steps or at least part of steps or stages in other steps.

It should be understood that the above embodiments are exemplary and are not intended to include all possible implementations included in the claims. Various modifications and changes may also be made on the basis of the above embodiments without departing from the scope of the present disclosure. Similarly, various technical features of the above embodiments may also be combined arbitrarily to form additional embodiments of the present disclosure that may not be explicitly described. Therefore, the above embodiments only express several implementations of the present disclosure and do not limit the protection scope of the present disclosure.

The invention claimed is:

1. A method for determining blood flow velocity using a dual die group, applied to a Doppler blood flow detection device, wherein the Doppler blood flow detection device comprises a first die group and a second die group placed at different positions of a blood vessel to be detected, the method comprises:
   obtaining a first spectrum waveform by detecting the blood vessel to be detected using the first die group;
   obtaining a second spectrum waveform by detecting the blood vessel to be detected using the second die group;
   determining a relationship between an actual Doppler angle during detection and a set Doppler angle in the Doppler blood flow detection device according to the first spectrum waveform and the second spectrum waveform;
   adjusting the first spectrum waveform and the second spectrum waveform according to the determined relationship, wherein the adjusting the first spectrum waveform and the second spectrum waveform according to the determined relationship comprises adjusting a first peak value of the first spectrum waveform and a second peak value of the second spectrum waveform to obtain a peak value corresponding to the adjusted first spectrum waveform and a peak value corresponding to the adjusted second spectrum waveform according to the following Equations:

$$Vm' = Vm1 * \cos\alpha / \cos(\alpha + r),$$

$$Vm2' = Vm2 * \cos\alpha / \cos(\alpha - r),$$

wherein, Vm1 represents the first peak value of the first spectrum waveform, Vm2 represents the second peak value of the second spectrum waveform, Vm1' represents the peak value corresponding to the adjusted first spectrum waveform, Vm2' represents the peak value corresponding to the adjusted second spectrum waveform, a represents a set Doppler angle, r represents a deviation angle between the actual Doppler angle during detection and α, and α+r and α−r represent the actual Doppler angles during the detection of the first die group and the second die group, respectively; and
   determining a blood flow velocity measurement value according to the adjusted first spectrum waveform and the adjusted second spectrum waveform.

2. The method for determining blood flow velocity using a dual die group according to claim 1, wherein the determining a relationship between an actual Doppler angle during detection and a set Doppler angle in the Doppler blood flow detection device according to the first spectrum waveform and the second spectrum waveform comprises:
　　determining the first peak value according to the first spectrum waveform;
　　determining the second peak value according to the second spectrum waveform; and
　　determining that the actual Doppler angle during detection and the set Doppler angle satisfy the following relationship according to the first peak value and the second peak value:

$$\cos(\alpha + r)/\cos(\alpha - r) = Vm1/Vm2.$$

3. The method for determining blood flow velocity using a dual die group according to claim 2, wherein the step of determining the first peak value according to the first spectrum waveform comprises:
　　determining a plurality of peak values in a plurality of cycles according to the first spectrum waveform;
　　eliminating an abnormal value from the plurality of peak values using Pauta criterion; and
　　calculating an average value of peak values remained after eliminating the abnormal value.

4. The method for determining blood flow velocity using a dual die group according to claim 2, wherein the step of determining the second peak value according to the second spectrum waveform comprises:
　　determining a plurality of peak values in a plurality of cycles according to the second spectrum waveform;
　　eliminating an abnormal value from the plurality of peak values using Pauta criterion; and
　　calculating an average value of peak values remained after eliminating the abnormal value.

5. The method for determining blood flow velocity using a dual die group according to claim 1, wherein a frequency of a signal emitted by the first die group and a frequency of a signal emitted by the second die group are in the range of 1 MHz-16 MHz.

6. The method for determining blood flow velocity using a dual die group according to claim 1, wherein a frequency F1 of a signal emitted by the first die group and a frequency F2 of a signal emitted by the second die group satisfy the following relationships:

$$F1 < F2,$$

a remainder of dividing F2 by F1 is greater than 0.5 MHz, and $$F2 < 3F1.$$

7. The method for determining blood flow velocity using a dual die group according to claim 1, wherein the Doppler blood flow detection device comprises a probe, and the first die group and the second die group are disposed within the probe, and the method further comprises:
　　determining a roll angle of the probe in a detection state, wherein the roll angle is an angle between a projection direction of a sound field emitted by an emitting die in the probe on a horizontal plane and a blood flow direction in the blood vessel to be detected, and the emitting die is in the first die group and/or the second die group; and
　　correcting the blood flow velocity measurement value according to the roll angle to obtain a corrected blood flow velocity measurement value.

8. The method for determining blood flow velocity using a dual die group according to claim 7, wherein the Doppler blood flow detection device further comprises an attitude sensor disposed within the probe, and the determining a roll angle of the probe in a detection state comprises:
　　determining the roll angle of the probe in the detection state using the attitude sensor.

9. The method for determining blood flow velocity using a dual die group according to claim 8, wherein the attitude sensor comprises a three-axis acceleration sensor, and the determining a roll angle of the probe in a detection state comprises:
　　obtaining acceleration components of gravity acceleration in directions of three mutually perpendicular coordinate axes in the detection state using the three-axis acceleration sensor, and determining the roll angle according to the acceleration components.

10. The method for determining blood flow velocity using a dual die group according to claim 8, wherein the attitude sensor comprises a gyroscope, and the determining a roll angle of the probe in a detection state comprises:
　　obtaining the roll angle in the detection state using the gyroscope.

11. The method for determining blood flow velocity using a dual die group according to claim 7, wherein the correcting the blood flow velocity measurement value according to the roll angle to obtain a corrected blood flow velocity measurement value comprises:
　　obtaining the corrected blood flow velocity measurement value according to the following Equation:

$$V1 = V/\sin\phi,$$

wherein, V1 represents the corrected blood flow velocity measurement value, V represents a blood flow velocity measurement value before being corrected, and $\phi$ represents the roll angle.

12. The method for determining blood flow velocity using a dual die group according to claim 1, wherein the obtaining a first spectrum waveform by detecting the blood vessel to be detected using the first die group comprises:
　　obtaining an emitting angle, wherein the emitting angle is an angle between a direction of emitting a signal by an emitting die in the first die group and a blood flow direction in the blood vessel to be detected;
　　obtaining a distance between the emitting die and a receiving die in a same die group in the Doppler blood flow detection device and a distance between the emitting die and the blood vessel to be detected;
　　determining a receiving angle according to the emitting angle, the distance between the emitting die and the receiving die, and the distance between the emitting die and the blood vessel to be detected, wherein the receiving angle is an angle between a direction of receiving a signal by the receiving die in the first die group and the blood flow direction; and
　　determining the first spectrum waveform according to the emitting angle and the receiving angle.

13. The method for determining blood flow velocity using a dual die group according to claim 12, wherein
the distance between the emitting die and the blood vessel to be detected comprises a first distance from the emitting die to the blood vessel to be detected along the direction of emitting the signal by the emitting die;
the determining a receiving angle according to the emitting angle, the distance between the emitting die and the receiving die, and the distance between the emitting die and the blood vessel to be detected comprises determining the receiving angle according to the following Equation:

$$|\beta - \alpha| = \arctan(D/L),$$

wherein, β represents the receiving angle, α represents the emitting angle, |β−α| represents an absolute value of a difference between the receiving angle and the emitting angle, D represents the distance between the emitting die and the receiving die, and L represents the first distance.

14. The method for determining blood flow velocity using a dual die group according to claim 13, wherein the obtaining a distance between the emitting die and the blood vessel to be detected comprises:
obtaining a duration from emitting the signal by the emitting die to receive the signal by the receiving die;
determining a propagation distance of the signal in the duration according to the duration and a propagation speed of the signal; and
determining the first distance according to the propagation distance.

15. The method for determining blood flow velocity using a dual die group according to claim 13, wherein the obtaining a distance between the emitting die and the blood vessel to be detected comprises:
obtaining a second distance input by a user based on an input device, wherein the second distance is a distance between the emitting die and the blood vessel to be detected in a direction perpendicular to a skin surface;
determining the first distance according to the second distance by the following Equation:

$$L = H/\sin\alpha,$$

wherein, H represents the second distance.

16. A Doppler blood flow detection device, wherein the Doppler blood flow detection device comprises a first die group, a second die group, and a signal processing module, and the Doppler blood flow detection device is configured to:
obtain a first spectrum waveform by detecting the blood vessel to be detected using the first die group;
obtain a second spectrum waveform by detecting the blood vessel to be detected using the second die group;
determine, by the signal processing module, a relationship between an actual Doppler angle during detection and a set Doppler angle in the Doppler blood flow detection device according to the first spectrum waveform and the second spectrum waveform;
adjust, by the signal processing module, the first spectrum waveform and the second spectrum waveform according to the determined relationship, wherein the adjust the first spectrum waveform and the second spectrum waveform according to the determined relationship comprises adjusting a first peak value of the first spectrum waveform and a second peak value of the second spectrum waveform to obtain a peak value corresponding to the adjusted first spectrum waveform and a peak value corresponding to the adjusted second spectrum waveform according to the following Equations:

$$Vm1'=Vm1*\cos\alpha/\cos(\alpha+r),$$

$$Vm2'=Vm2*\cos\alpha/\cos(\alpha-r),$$

wherein, Vm1 represents the first peak value of the first spectrum waveform, Vm2 represents the second peak value of the second spectrum waveform, Vm1' represents the peak value corresponding to the adjusted first spectrum waveform, Vm2' represents the peak value corresponding to the adjusted second spectrum waveform, α represents a set Doppler angle, r represents a deviation angle between the actual Doppler angle during detection and α, and α+r and α−r represent the actual Doppler angles during the detection of the first die group and the second die group, respectively; and
determine a blood flow velocity measurement value according to the adjusted first spectrum waveform and the adjusted second spectrum waveform.

17. The method for determining blood flow velocity using a dual die group according to claim 1, wherein the obtaining a second spectrum waveform by detecting the blood vessel to be detected using the second die group comprises:
obtaining an emitting angle, wherein the emitting angle is an angle between a direction of emitting a signal by an emitting die in the second die group and a blood flow direction in the blood vessel to be detected;
obtaining a distance between the emitting die and a receiving die in a same die group in the Doppler blood flow detection device and a distance between the emitting die and the blood vessel to be detected;
determining a receiving angle according to the emitting angle, the distance between the emitting die and the receiving die, and the distance between the emitting die and the blood vessel to be detected, wherein the receiving angle is an angle between a direction of receiving a signal by the receiving die in the second die group and the blood flow direction; and
determining the second spectrum waveform according to the emitting angle and the receiving angle.

* * * * *